(12) United States Patent
Wilkins, Jr.

(10) Patent No.: US 6,420,435 B1
(45) Date of Patent: Jul. 16, 2002

(54) METHOD FOR TREATING GASTROINTESTINAL DISORDERS

(76) Inventor: Joe S. Wilkins, Jr., 7700 Seawall Blvd., Unit 403, Galveston, TX (US) 77551

( * ) Notice: Subject to any disclaimer, the term of this patent is extended or adjusted under 35 U.S.C. 154(b) by 0 days.

(21) Appl. No.: 09/689,151

(22) Filed: Oct. 12, 2000

Related U.S. Application Data

(60) Provisional application No. 60/162,831, filed on Nov. 1, 1999.

(51) Int. Cl.[7] .............................................. A61K 31/015
(52) U.S. Cl. ..................... 514/763; 514/819; 514/925; 514/926; 514/927
(58) Field of Search ................................ 514/763, 819, 514/925, 926, 927

(56) References Cited

U.S. PATENT DOCUMENTS

| | | | |
|---|---|---|---|
| 3,882,248 A | 5/1975 | Igimi et al. | |
| 4,338,251 A | 7/1982 | Sato et al. | |
| 4,435,423 A | 3/1984 | Sato et al. | |
| 4,468,458 A | 8/1984 | Sato et al. | |
| 4,595,694 A | 6/1986 | Takase et al. | |
| 4,675,313 A | 6/1987 | Arias | |
| 4,888,417 A | 12/1989 | Shiraga et al. | |
| 5,153,229 A | 10/1992 | Chastain et al. | |
| 5,229,425 A | 7/1993 | Chastain et al. | |
| 5,270,344 A | 12/1993 | Herman | |
| 5,308,872 A | 5/1994 | Chastain et al. | |
| 5,308,873 A | 5/1994 | Chastain et al. | |
| 5,543,435 A | 8/1996 | Chastain et al. | |
| 5,889,049 A | 3/1999 | Juergens | |
| 6,294,586 B1 * | 9/2001 | Yelle et al. ................. 514/338 |

FOREIGN PATENT DOCUMENTS

| | | |
|---|---|---|
| GB | 2135990 A | 9/1984 |
| JP | 356113718 A | 9/1981 |
| JP | 361271297 A | 12/1986 |
| JP | 62174035 A2 | 7/1987 |
| JP | 1066115 A | 3/1989 |
| JP | 402142743 A | 5/1990 |
| JP | 10226640 A | 8/1998 |

OTHER PUBLICATIONS

U.S. patent application 2001/0021403 (Sep. 13, 2001).
Chemical Abstracts printout—Van Lieshout, E.M., et al., Effects of Dietary Anticarcinogens on Rat Gastrointestinal Glutathione Peroxidase Activity, 5(4) *Oncol. Rep.*, 959–963 (1998).
Chemical Abstracts printout—Van Lieshout, E.M., et al., Effects of Sulforaphane Analog Compound 30, Indole–3–Carbinol, d–Limonene or relafen on Glutathione S–transfereases and Glutathione Peroxidase of the Rate Digestive Tract, 1379(3) *Biochim. Biophys. Acta*, 325–336 (1998).
Chemical Abstracts printout—Rodriguez, A.M., et al., "Structure–Activity Relationship of Limonene Derivatives Acting as Gastric Cytoprotextive Agents," 82(5) *An. Asoc. Quim, Argent.*, 399–414 (1994).
Chemical Abstracts printout—Van Lieshout, E.M., et al., Effects of Dietary Anticarcinogens on Rat Gastrointestinal Glutathione S–Transferase Theta 1–1 Levels, 19(11) *Carcinogenesis*, 2055–2057 (1998).

* cited by examiner

*Primary Examiner*—Frederick Krass
(74) *Attorney, Agent, or Firm*—Laura Barrow

(57) ABSTRACT

Methods of treating gastrointestinal disorders (e.g. heart bum, GERD, and gastric indigestion) comprising orally administering therapeutically effective amounts of limonene are described herein.

41 Claims, 4 Drawing Sheets

METHOD FOR TREATING GASTROINTESTINAL DISORDERS

This is application claims the benefit of the filing of now abandoned U.S. provisional application serial No. 60/162,831, filed Nov. 1, 1999, which is incorporated by reference herein in its entirety.

SUMMARY OF THE INVENTION

The present invention is directed to a method for treating gastrointestinal disorders and in particular comprises the oral administration of a therapeutically effective amount of limonene, preferably a purified form of d-limonene, to a person in need of such treatment.

DETAILED DESCRIPTION OF THE PREFERRED EMBODIMENT

Figure 1:
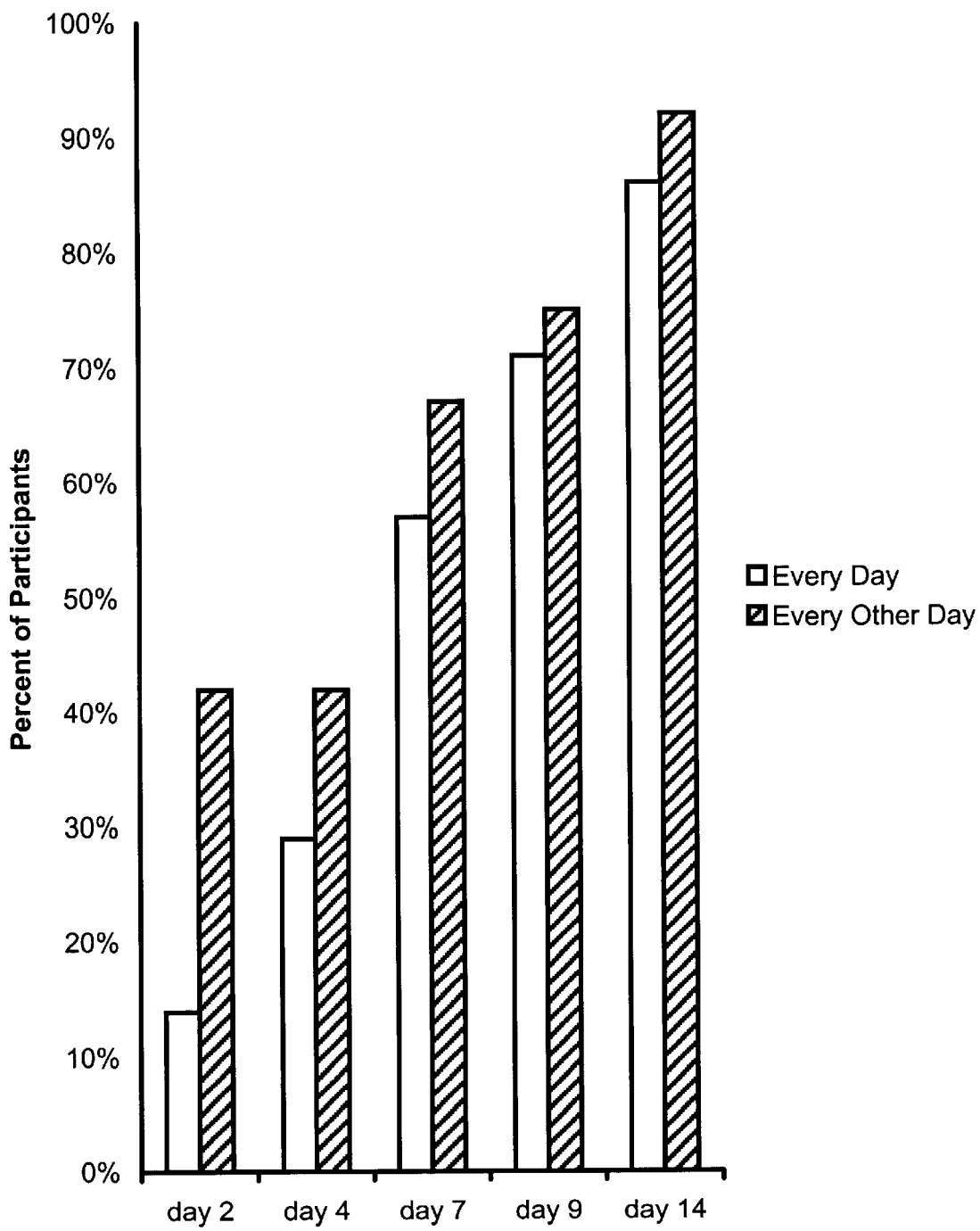
FIG. 1 is a bar graph comparing every day vs. every other day treatment regimens with d-limonene.
Figure 2:
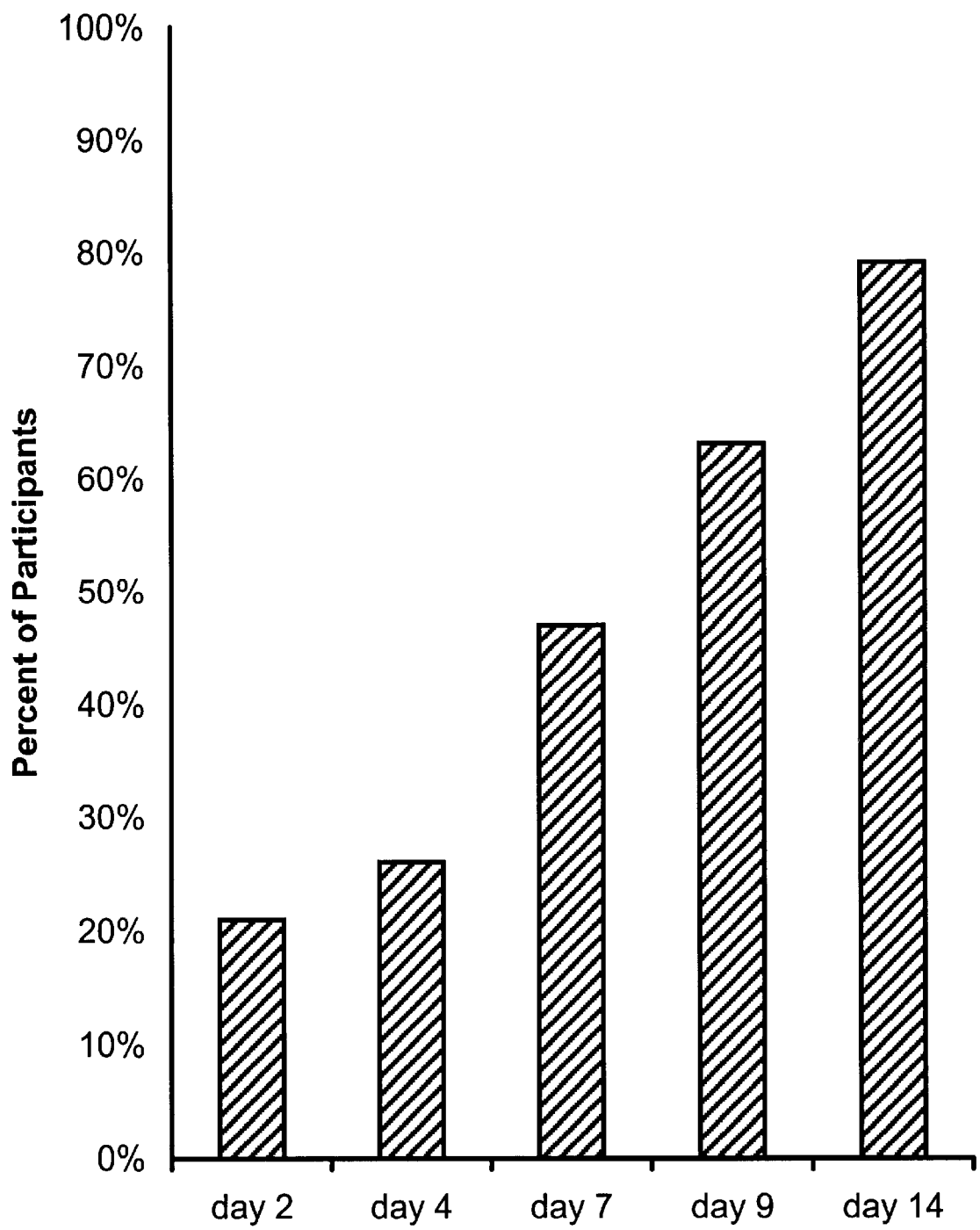
FIG. 2 is a bar graph showing percentage of participants having a severity of symptoms rating=1 over a 14-day treatment with d-limonene.

The present invention is directed to a method for treating gastrointestinal disorders and comprises the oral administration of a therapeutically effective amount of limonene, preferably a purified form of d-limonene (i.e. at least 98%), to a person in need of such treatment. "Limonene" as used herein shall include both d-limonene and 1-limonene. While the mechanism of action is not certain at this time, in vitro studies suggest that this compound has a neutralizing effect on gastric acid by coating the stomach wall and thereby protecting the mucosal lining from gastric juices. The inventor has discovered that oral administration of a therapeutically effective amount of purified, food grade limonene (preferably at least 98% pure d-limonene), taken once daily or once every other day for 2 to 20 days, will alleviate or eliminate entirely the symptoms, both in terms of frequency and severity, of gastrointestinal disorders, such disorders ranging from mild/moderate heartburn and gastric indigestion to severe heartburn or gastro esophageal reflux disorder (GERD).

The therapeutic regimen for treating gastrointestinal disorders, as defined further below, comprises the oral administration of a therapeutically effective amount of limonene, wherein the limonene is administered once a day or once every other day for a time sufficient to alleviate or eliminate entirely the severity and frequency of the gastrointestinal symptoms, such symptoms including stomach pain, burping, and gastric acid reflux. As used herein, "treatment" shall mean temporary or permanent alleviation or elimination of gastrointestinal disorder symptoms. A preferred adult dose of limonene is about 500 to 1,000 milligrams administered once daily or once every other day for 7–20 days. It will be appreciated by those of ordinary skill in the art that the amount of limonene, dosing schedule, and duration of treatment may vary depending upon the individual's age, weight, and severity of the gastrointestinal disorder.

A preferred pharmaceutical formulation is a gelatin capsule, although the limonene may be formulated in suspension, emulsion, or solution. Alternatively, the limonene may be orally administered as the natural oil.

The present invention is particularly useful in alleviating the severity and frequency of gastrointestinal disorders. In many cases, it has been found that the gastrointestinal disorder symptoms disappear entirely for long periods of time, from weeks to months, in fact, without any recurrence, or only minor recurrences, of the symptoms. As used herein, "gastrointestinal disorder" shall mean mild/moderate heartburn, stomach acid indigestion, and severe heartburn/GERD. It should be noted, however, that recent studies have found that the treatment regimens described herein are not effective on persons suffering from diagnosed peptic ulcers. In fact, ulcer sufferers who have taken the 1,000 mg dose regimen of d-limonene as described herein experienced an increase in the severity of gastrointestinal symptoms and consequently had to discontinue the treatment regimen.

The inventor, who has had a long history of severe heartburn, has discovered that when he has taken limonene (from 500 mg to 1000 mg) every other day for 8–20 days, the severity and frequency of his symptoms were alleviated permanently. Similar results were obtained on another adult taking 1000 mg every other day as well as on participants of studies discussed in more detail in Examples 1–2.

It has further been discovered by the inventor that administering limonene having at least a 98% purity significantly reduced certain side effects, such as diarrhea and headache, experienced by some individuals. Any conventional distillation method known by those of ordinary skill in the art for obtaining a highly purified form of d-limonene (about 98% pure) may be employed. Example 3 illustrates one preferred distillation method for removing the majority of contaminants.

EXAMPLE 1

Initial studies of the inventive treatment regimen were conducted at different times on 19 adults suffering from chronic heartburn or gastroesophagael reflux disorder (GERD). All of the participants had a previous history of chronic heartburn or GERD, ranging in a severity of mild/moderate to severe, for at least a period of five years. Thirty-seven (37%) of the total participants in these initial studies were male ranging in age from 42 to 73 years (average age=50 years), while sixty-three (63%) of the participants were female ranging in age from 34 to 70 years (average age=43). All of the participants discontinued using their respective treatments of choice (i.e. over-the-counter (OTC) and/or prescription medications) at least one day prior to beginning the inventive treatment regimen. Prior to beginning the treatment regimen, each participant was asked to rate the frequency and severity of his/her gastrointestinal disorder symptoms on a scale of 1–10. For "severity of symptoms," 1 corresponded to complete relief of symptoms while 10 corresponded to severe, painful symptoms. A rating of 2 would correspond to mild symptoms. For "frequency of symptoms," 1 corresponded to complete relief of symptoms while 10 corresponded to daily symptoms. Prior to beginning the treatment regimen, all but one of the participants had a severity rating of 5 or greater (one participant had a rating of 3). All but two participants had a frequency rating of 5 or greater (two participants had a rating of 2).

Eleven of the participants were administered 1 capsule of d-limonene every other day for 20 days. Five of the participants were administered 1 capsule of d-limonene every day for 16 to 20 days. Each capsule contained 1000 mg of d-limonene having a purity of from 98.5% to 99.3%.

Figure 3:
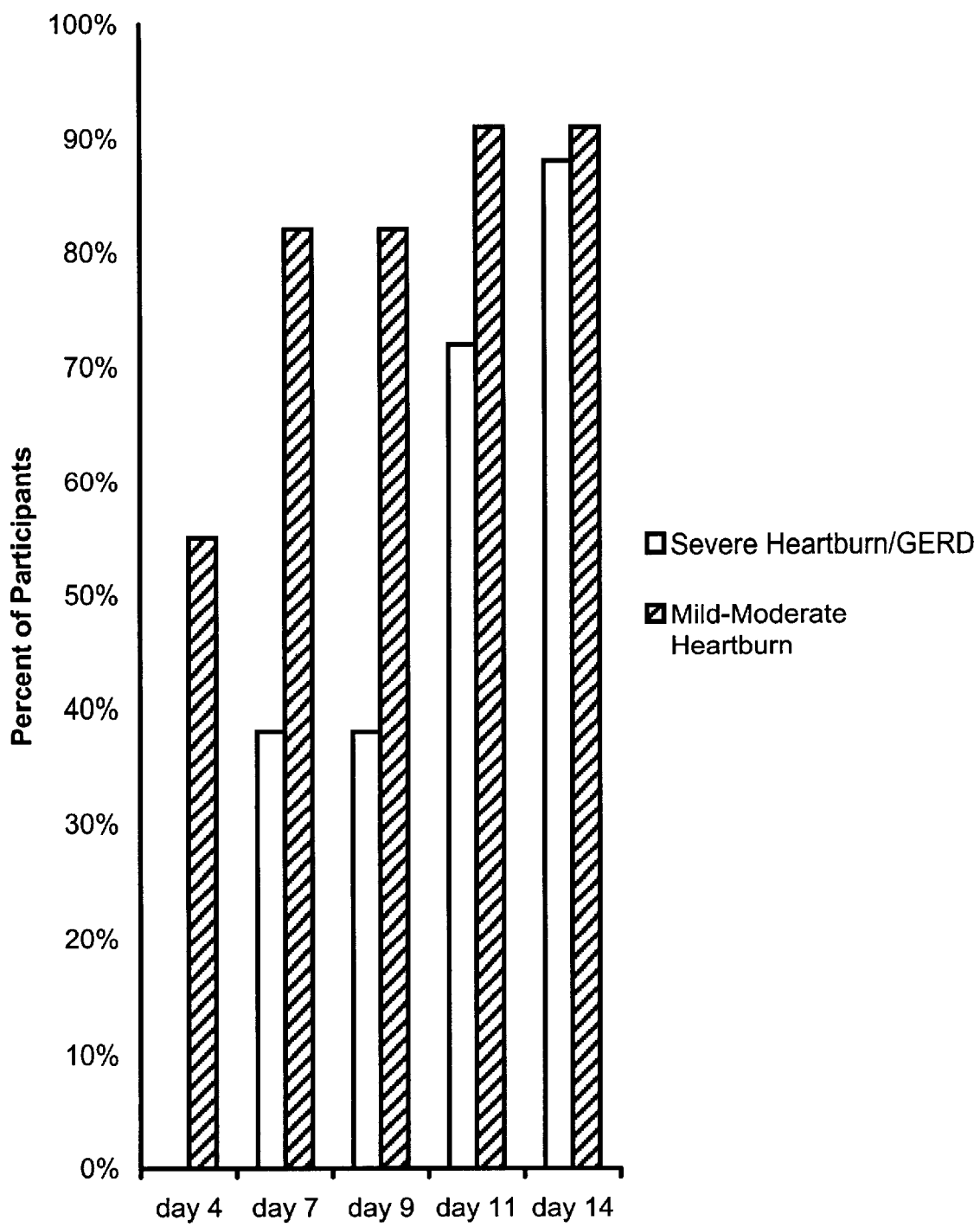
FIG. 3 is a bar graph comparing the effectiveness of the inventive treatment regimen between those suffering from mild gastrointestinal disorders and those suffering from severe gastrointestinal disorders.

Table 1 shows the pre-treatment severity and frequency ratings for the participants in each of the treatment regimens. Table 2 shows the percentage of participants experiencing complete relief or a severity rating=1–2 at different days through the treatment period for the different treatment regimens (i.e. every day and every other day). FIG. 1 is a graph illustrating the data shown in Table 2. FIG. 3 is a graph illustrating the percentage of all the participants (i.e. those undergoing the every other day regimen and every day regimen) having a severity rating of 1.

TABLE 1

Pre-Study Symptom Ratings

|  | Avg. Severity | Range (Severity) | Ave. Freq. | Range (Freq.) |
|---|---|---|---|---|
| Every day regimen | 8 | 5–10 | 8.1 | 6–10 |
| Every other day regimen | 7.9 | 3–10 | 7.4 | 2–9 |
| Overall | 7.8 | 3–10 | 7.3 | 2–10 |

TABLE 2

Post Treatment Regimen Symptom Ratings

|  | Day 2 | Day 4 | Day 7 | Day 9 | Day 14 |
|---|---|---|---|---|---|
| % of all participants with symptom rating = 1–2 | 32% | 32% | 63% | 74% | 89% |
| % of participants (every day regimen) with symptom rating = 1–2 | 14% | 29% | 57% | 71% | 86% |
| % of participants (every other day regimen) with symptom rating = 1–2 | 42% | 42% | 67% | 75% | 92% |

When comparing the results of all of the participants, about 20% achieved complete relief of symptoms (rating of 1) as early as day 2 of their regimen. The percentage of participants achieving complete relief of symptoms gradually increased over time, with 79% of the participants achieving complete relief by day 14. About 32% of the total participants achieved significant relief (rating 1–2) by day 2 with an increase to 89% of participants experiencing complete symptom relief or severity rating of 1–2 by day 14.

In comparing the two treatment regimens (i.e. every other day vs. every day), it was discovered that those taking one gram of d-limonene every other day experienced earlier symptom relief with a higher percentage of participants (about 92%) experiencing complete relief by day 14.

Table 3 and FIG. 3 compare the percentage of total participants suffering from severe heartburn or GERD vs. those participants suffering from mild/moderate heartburn who experienced "severity" and "frequency" symptom ratings of 1–2. Results showed that those with mild/moderate heartburn experienced symptom relief sooner than those suffering from more severe heatburn/GERD; however, the final outcome by day 14 was about the same.

TABLE 3

| Pre-Study Symptoms | Day 4 | Day 7 | Day 9 | Day 11 | Day 15 |
|---|---|---|---|---|---|
| Severe heartburn/ GERD group | 0% | 38% | 38% | 72% | 88% |
| Mild/moderate heartburn group | 55% | 82% | 82% | 91% | 91% |

EXAMPLE 2

Figure 4:
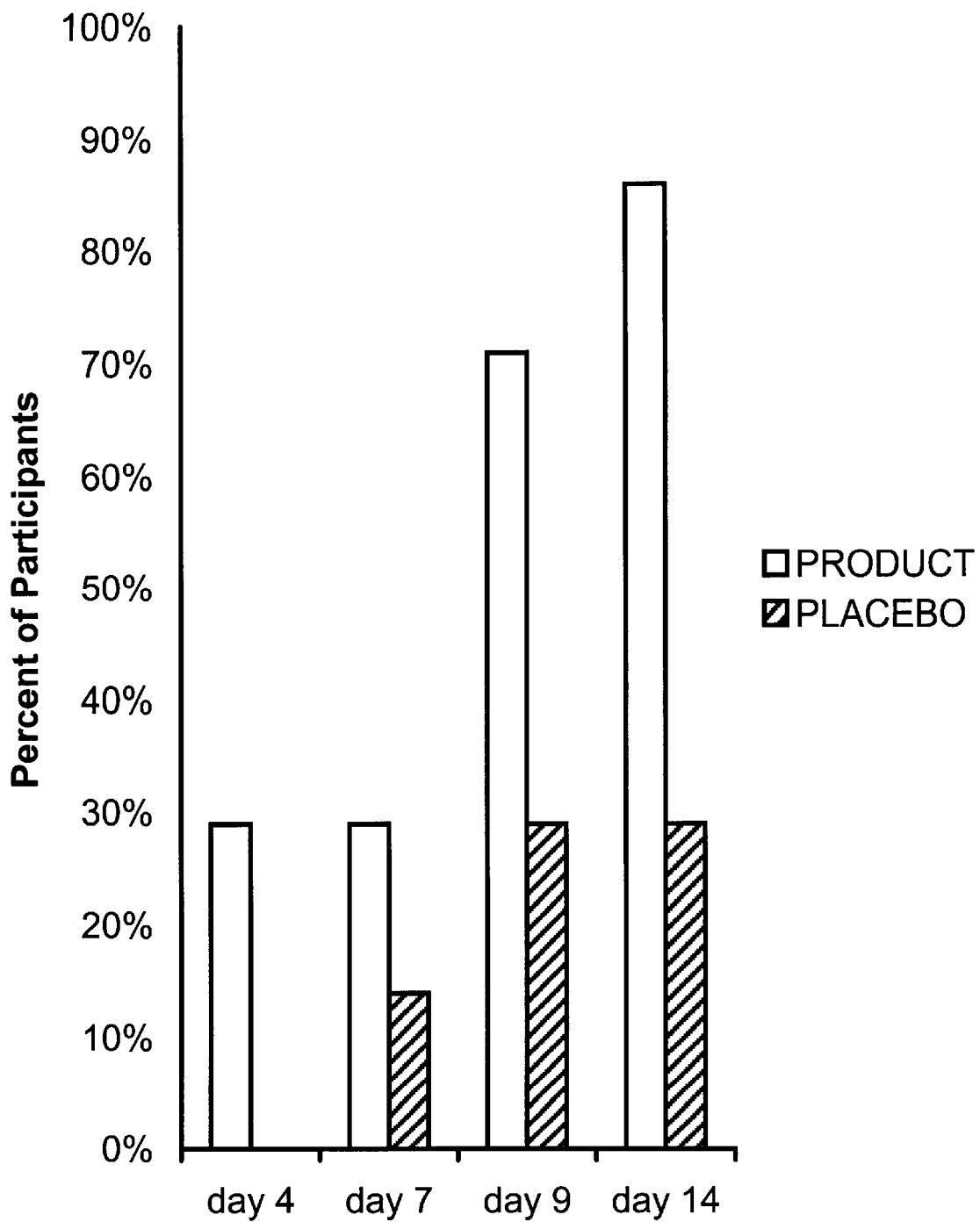
FIG. 4 is a bar graphs comparing d-limonene product vs. placebo results from a double-blind study over a 14-day period of treatment.

A preliminary double-blind placebo study was conducted on 13 participants suffering from mild/moderate heartburn to severe heartburn/GERD. Seven participants were administered the product and six were administered a placebo. In the "limonene" group (i.e. 1 capsule containing 1 gram of 98% d-limonene), two participants were administered 1 capsule every day for five days followed by 1 capsule every other day for five days. The remaining "limonene" group participants were administered 1 capsule every other day for 20 days. In the "placebo" group, three participants were administered 1 placebo capsule (i.e. gelatin capsule containing soybean oil) daily for five days, followed by 1 capsule every other day for 5 days. Two participants were administered 1 placebo capsule every other day for 20 days while one participant having severe heartburn was administered 1 placebo capsule twice a day for 5 days, followed by 1 capsule every day for 5 days, followed by 1 capsule as needed. As shown in Table 4 (and FIG. 4), a significant difference in results was obtained between the two groups (n=14).

TABLE 4

Product vs. Placebo

| Compound | Day 4 | Day 7 | Day 9 | Day 14 |
|---|---|---|---|---|
| d-limonene product | 29% | 29% | 71% | 86% |
| Placebo | 0% | 14% | 29% | 29% |

EXAMPLE 3

An atmospheric distillation unit was charged with 100 milliliters of 96–96.5% Food Grade limonene. The distillation unit was operated with a reflux ratio of 1:1. The desired limonene distillate was removed in a range of from about 340° F. to 390° F. and was of a purity of about 98%.

I claim:

1. A method for the treatment of gastrointestinal disorders, said method comprising orally administering to a person in need of such treatment a therapeutically effective amount of limonene.

2. The method of claim 1, wherein said gastrointestinal disorder is selected from the group consisting of heartburn, gastro esophageal reflux disorder, and gastric indigestion.

3. The method of claim 2, wherein said amount of limonene is from about 500 mg to about 1000 mg administered every day to said person for at least two days.

4. The method of claim 3, wherein said amount is 1000 mg.

5. The method of claim 2, wherein said amount of limonene is from about 500 mg to about 1000 mg administered every other day to said person for at least four days.

6. The method of claim 5, wherein said amount is 1000 mg.

7. The method of claim 2, wherein said amount of limonene is from about 500 mg to about 1000 mg administered every day to said person for at least 7 days.

8. The method of claim 7, wherein said amount is 1000 mg.

9. The method of claim 2, wherein said amount of limonene is from about 500 mg to about 1000 mg administered every day to said person for 14 to 20 days.

10. The method of claim 9, wherein said amount is 1000 mg.

11. The method of claim 2, wherein said amount of limonene is from about 500 mg to about 1000 mg administered every other day to said person for at least 7 days.

12. The method of claim 11, wherein said amount is 1000 mg.

13. The method of claim 2, wherein said amount of limonene is from about 500 mg to about 1000 mg administered every other day to said person for 14 to 20 days.

14. The method of claim 13, wherein said amount is 1000 mg.

15. A method of treating gastrointestinal disorders, said method comprising orally administering to a person in need of such treatment a therapeutically effective amount of limonene, wherein said limonene has a purity of at least 98%.

16. The method of claim 15, wherein said gastrointestinal disorder is selected from the group consisting of heartburn, gastro esophageal reflux disorder, and gastric indigestion.

17. The method of claim 16, wherein said amount of limonene is from about 500 mg to about 1000 mg administered every day to said person for at least two days.

18. The method of claim 17, wherein said amount is 1000 mg.

19. The method of claim 16, wherein said amount of limonene is from about 500 mg to about 1000 mg administered every other day to said person for at least four days.

20. The method of claim 19, wherein said amount is 1000 mg.

21. The method of claim 16, wherein said amount of limonene is from about 500 mg to about 1000 mg administered every day to said person for at least 7 days.

22. The method of claim 21, wherein said amount is 1000 mg.

23. The method of claim 16, wherein said amount of limonene is from about 500 mg to about 1000 mg administered every day to said person for 14 to 20 days.

24. The method of claim 23, wherein said amount is 1000mg.

25. The method of claim 16, wherein said amount of limonene is from about 500 mg to about 1000 mg administered every other day to said person for at least 7 days.

26. The method of claim 25, wherein said amount is 1000mg.

27. The method of claim 16, wherein said amount of limonene is from about 500 mg to about 1000 mg administered every other day to said person for 14 to 20 days.

28. The method of claim 27, wherein said amount is 1000 mg.

29. A method of treating gastrointestinal disorders selected from the group consisting of heartburn, gastro esophageal reflux disorder, and gastric indigestion, wherein said method comprises orally administering to a person in need of such treatment a therapeutically effective amount of d-limonene having a purity of at least 98%.

30. The method of claim 29, wherein said amount of limonene is from about 500 mg to about 1000 mg administered every day to said person for at least two days.

31. The method of claim 30, wherein said amount is 1000 mg.

32. The method of claim 29, wherein said amount of limonene is from about 500 mg to about 1000 mg administered every other day to said person for at least four days.

33. The method of claim 32, wherein said amount is 1000 mg.

34. The method of claim 29, wherein said amount of limonene is from about 500 mg to about 1000 mg administered every day to said person for at least 7 days.

35. The method of claim 34, wherein said amount is 1000 mg.

36. The method of claim 29, wherein said amount of limonene is from about 500 mg to about 1000 mg administered every day to said person for 14 to 20 days.

37. The method of claim 36, wherein said amount is 1000 mg.

38. The method of claim 29, wherein said amount of limonene is from about 500 mg to about 1000 mg administered every other day to said person for at least 7 days.

39. The method of claim 38, wherein said amount is 1000 mg.

40. The method of claim 29, wherein said amount of limonene is from about 500 mg to about 1000 mg administered every other day to said person for 14 to 20 days.

41. The method of claim 40, wherein said amount is 1000 mg.

* * * * *